United States Patent
Hihath et al.

(10) Patent No.: US 11,828,745 B2
(45) Date of Patent: Nov. 28, 2023

(54) ON-CHIP PLATFORM FOR SINGLE-MOLECULE ELECTRICAL CONDUCTANCE MEASUREMENTS

(71) Applicant: THE REGENTS OF THE UNIVERSITY OF CALIFORNIA, Oakland, CA (US)

(72) Inventors: Joshua Hihath, Woodland, CA (US); Xiaoguang Liu, Davis, CA (US); Maria Louise Marco, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 310 days.

(21) Appl. No.: 17/211,338

(22) Filed: Mar. 24, 2021

(65) Prior Publication Data

US 2021/0255164 A1    Aug. 19, 2021

Related U.S. Application Data

(60) Division of application No. 15/646,956, filed on Jul. 11, 2017, now Pat. No. 10,989,705, which is a
(Continued)

(51) Int. Cl.
*G01N 33/487* (2006.01)
*C12Q 1/68* (2018.01)
*G01N 33/483* (2006.01)

(52) U.S. Cl.
CPC ......... *G01N 33/48721* (2013.01); *C12Q 1/68* (2013.01); *G01N 33/483* (2013.01)

(58) Field of Classification Search
CPC ... G01N 33/48721; G01N 33/483; C12Q 1/68
See application file for complete search history.

(56) References Cited

U.S. PATENT DOCUMENTS

2003/0080042 A1*   5/2003   Barth ................ B01D 67/0058
                                                                    216/2

OTHER PUBLICATIONS

Brouwer, Dannis Michel, et al. "MEMS-based clamp with a passive hold function for precision position retaining of micro manipulators." Journal of micromechanics and microengineering 19.6 (2009): 065027. (Year: 2009).*

(Continued)

*Primary Examiner* — Robert J Eom
(74) *Attorney, Agent, or Firm* — Park, Vaughan, Fleming & Dowler LLP

(57) ABSTRACT

A micro-electromechanical platform and array system and methods for identifying microbial species with single molecule electrical conductance measurements are provided. The electromechanical platform has a two-tier actuation mechanism with a long stroke provided by a comb drive and a fine stroke provided by an in-plane flexural actuator. The platform is capable of making contact with a single-molecule, applying a bias, measuring the current, and performing a large number of measurements for statistical analysis. The system is capable of detecting any microbial species without requiring enzymatic amplification by detecting specific RNA sequences, for example. With oligonucleotide target molecules, the conductance is extremely sensitive to the sequence so even single-nucleotide polymorphisms can be identified. The system can also discern between subspecies using the same DNA probe. The system provides reliable, efficient, and inexpensive detection and species-level identification of microorganisms in complex detecting environments.

20 Claims, 6 Drawing Sheets

Related U.S. Application Data continuation of application No. PCT/US2016/014116, filed on Jan. 20, 2016.

(60) Provisional application No. 62/105,688, filed on Jan. 20, 2015.

(56) References Cited

OTHER PUBLICATIONS

Yamahata, Christophe, et al. "Silicon nanotweezers with subnanometer resolution for the micromanipulation of biomolecules." Journal of microelectromechanical systems 17.3 (2008): 623-631. (Year: 2008).*
Lafitte, Nicolas, et al. "Improvement of silicon nanotweezers sensitivity for mechanical characterization of biomolecules using closed-loop control." IEEE/ASME Transactions on Mechatronics 20.3 (2014): 1418-1427. (Year: 2014).*

\* cited by examiner

ON-CHIP PLATFORM FOR SINGLE-MOLECULE ELECTRICAL CONDUCTANCE MEASUREMENTS

CROSS-REFERENCE TO RELATED APPLICATIONS

This application is a divisional application of, and hereby claims priority under 35 U.S.C. § 120 to, pending U.S. patent application Ser. No. 15/646,956, entitled "On-Chip Platform for Single-Molecule Electrical Conductance Measurements," by inventors Joshua Hihath, et al., which was filed on 11 Jul. 2017, incorporated herein by reference in its entirety. U.S. patent application Ser. No. 15/646,956 is a 35 U.S.C. § 111(a) continuation of PCT international application number PCT/US2016/014116 filed on Jan. 20, 2016, incorporated herein by reference in its entirety, which claims priority to, and the benefit of, U.S. provisional patent application Ser. No. 62/105,688 filed on Jan. 20, 2015, incorporated herein by reference in its entirety. Priority is claimed to each of the foregoing applications.

BACKGROUND

1. Technical Field

The present technology pertains generally to devices and methods for detecting and identifying biological organisms or gene expression, and more particularly to an apparatus with an micro-electromechanical system (MEMS) that can be used to measure the conductance of a single molecule and is capable of identifying a microbial species, for example, by detecting specific nucleic acid sequences or other biomolecules using electrical conductance measurements.

2. Background

The ability to reliably detect and identify specific microorganisms including bacteria, viruses, and fungi is important for determining the presence of pathogens in food supplies, protecting crops, identifying diseases, tracking pandemics, and monitoring the human microbiome. Immunological and DNA detection methods are currently the two most prevalent microbial detection systems for both clinical and agricultural applications.

Immunology detection methods target cell surfaces or secreted antigens that are produced by target cells. Enzyme-linked immunoabsorbant assay (ELISA) is the most common example of an immunologically-based method. Immune-adsorption on beads is also an emerging technique. These approaches focus on recognizing the binding of antibodies or antigens to a complementary binding agent and typically require some labeling or enzymatic reaction to cause fluorescence or a color change in solution to read out the presence of the microbe optically. Although these techniques are quite powerful for recognizing the presence of a microbe, they are also prone to false positives as many microbial species produce similar antigens that may bind to the probe.

Another common method of identifying microbes is based on sequencing DNA. DNA-targeted assays primarily encompass various PCR (Polymerase Chain Reaction) methods including qPCR (quantitative Real-Time PCR) and bead-based methods. These techniques are based on amplification of the initial target sequences using PCR, and require multiple temperature cycles to obtain a reliable signal. To overcome the limitations of temperature cycling, loop-mediated isothermal amplification (LAMP) and related approaches have now been commercialized. LAMP maintains a constant temperature near 60° C. but still uses polymerases to amplify the starting material.

One significant drawback is that these techniques require multiple amplification steps using PCR, and techniques, like qPCR, require complex protocols, a large number of reagents, a mechanism for labeling the products, and a system for optically reading sequence information. Moreover, many of these techniques rely on multiple assays to positively identify distinct pathogens down to the strain or serotype level. The necessity of running multiple independent assays drastically increases the process time and the cost.

Alternatively, RNA detection is another technique for microbial detection, which has some key advantages. First, RNA is much more abundant in cells than genomic DNA, and secondly, many viruses important to human and plant health do not possess DNA, but instead use RNA to store genetic information. As such, RNA is an attractive target for microbe identification. However, despite these advantages, detection and identification of RNA targets typically follows a process similar to that used for DNA and requires the further step of reverse transcription prior to amplification. RNA is typically quantified by Reverse-Transcription quantitative PCR (RT-qPCR), although isothermal methods such as nucleic acid sequence-based amplification (NASBA) methods are also available.

With the importance microbe detection, and the drawbacks of current techniques, the development of robust new technologies that are capable of rapidly identifying specific microbial species inexpensively and reliably are needed.

BRIEF SUMMARY

The present technology provides a sensing platform utilizing an on-chip micro-electromechanical system (MEMS) that is capable of measuring the conductance of a single-molecule by repeatedly bringing two nanostructured electrodes into and out of contact with sub-angstrom precision. The movement of the electrodes on the chip can use electrical, magnetic, thermal, electrothermal, and piezoelectric actuation schemes or a combination of thereof. This procedure can be repeated to extract statistically significant information about the electrical properties of target molecules.

This apparatus and system can be used to measure the conductance of nucleic acid sequences or other relevant biological molecules. The system can also be used for detecting microbial species, examining or monitoring gene expression, identifying or detecting specific nucleic acid sequences from any species, detecting cancer markers, etc. Beyond biomolecules, the system can be used to interrogate other organic molecules of interest for fields such as molecular electronics. It can be used to test single-molecule diodes and wires and single-molecule transistors by adding an additional electrode.

The core of the preferred MEMS-based sensor platform consists of two parts, both of which are preferably made from silicon-on-insulator wafers. The first part comprises a movable electrode with at least one sharp conductive tip that can move linearly. The second part is a second electrode that is stationary. The conductive needle can be moved by MEMS-based actuators to make contact with a smooth surface of the second electrode for break junction measurements. The needle of the first electrode is preferably coated with a gold, platinum or titanium thin film and is electrically connected to the external circuit with signal traces patterned on the MEMS actuator. Although a moveable and a stationary electrode are preferred, two moveable electrodes could be used in the alternative with aligned conductive tips brought together and apart by the actuators.

In order to accurately measure the conductance of a single-molecule, the first electrode of the MEMS actuator platform needs a relatively large actuation stroke in the range of about 10 µm to 100 µm to bring the conductive tip in proximity of the second electrode. The platform also needs an extremely fine movement of a few angstroms to allow contact of the tip with the target molecules that ultimately come in contact with the second electrode.

To accommodate such a large dynamic range to the moveable electrode, a two-tier actuation mechanism is used in the preferred embodiment. The first tier is a comb drive to provide the large stroke and the second tier is an in-plane flexural actuator to provide the fine resolution. In one embodiment, two comb drive actuators are implemented into the system to achieve bidirectional linear movement. This system is used to move the entire tip-carriage into and out of the range of the flexural system for fine control movement and break-junction tapping cycles. The platform is also amenable to multiplexing and easy integration with electronics for field-deployable devices and high-throughput applications.

Because the system is capable of interrogating electronic properties of molecular systems at the single-molecule level, it has the potential for use as a chemical characterization platform for organic molecules. For example, the device has applications in microbial detection and identification by measuring the conductance duplexed oligonucleotide sequences that are specific to certain bacterial, viral, fungi and other microbial species.

Microbial detection and identification is often based on coupling optical readout mechanisms with either enzymatic amplification of DNA or immunological binding assays. Most techniques for identifying microbial species using DNA or RNA require Polymerase Chain Reaction (PCR) amplification of the oligonucleotides before enough material is present to detect the target oligonucleotide sequences. The multiple independent steps and tests of these techniques greatly increase the processing time and cost for detection and identification.

In contrast, the device will electrically detect and identify bacterial and viral RNA sequences, for example, without the necessity of using enzymatic amplification methods or fluorescent markers. In cases where microbe densities are particularly low, the device and methods provide additional sensitivity that allows for the target molecules to be detected in small quantities and the ability to differentiate closely related variants of a given bacterial or viral species or strain. This technology provides a quick, efficient, and inexpensive bacterial and viral detection and identification system. It also provides a quick and reliable method for demonstrating multiple and single-base mismatches.

To illustrate the technology, a single MEMS based break-junction (MEMS-BJ) platform with sub-angstrom mechanical control is used to measure the conductance of single RNA:DNA hybrid molecules to directly identify microbes of interest. In this illustration, the process begins by lysing and extracting RNA from a sample of interest. Then DNA probes with chemical linkers capable of binding to gold electrodes that are complementary to species-specific RNA fragments are added and all single-stranded material is digested. Target RNA fragments will hybridize with complementary DNA sequences that are capable of binding to the gold electrodes. This mixture is then introduced into the MEMS-based break-junction device and single-molecule conductance measurements are rapidly performed in complex sensing environments. When a DNA duplex binds to both electrodes, steps appear in the current vs. distance trace. Once several hundred conductance measurements are performed a conductance histogram verifying the molecule of interest is present can be obtained. Because the conductance is sensitive to single-nucleotide polymorphisms, this technique is capable of strain-level identification of microbes.

The ability to rapidly detect specific microbes in a complex sensing environment without requiring enzymatic amplification will directly impact the ability to identify potential pathogens in the food supply like *E. coli* or *Salmonella* as well as beneficial microorganisms incorporated into food such as *Lactobacillus plantarum*. However, this capability will also have broad impacts across the biological sciences, health-care, and national security. Anywhere where it is necessary to quickly and unambiguously detect particular microbial species in a complex environment will benefit from this instrumentation. Moreover, this device will have impacts beyond detection in arenas where the ability to electrically measure a single-molecule is important including charge-transport processes in proteins, single-molecule chemistry and physics, and molecular electronics.

Another aspect of the technology is to provide a sensing platform that removes the need for enzymatic amplification (i.e., PCR) or fluorescent markers.

Another aspect of the technology is to provide a platform for the detection and identification of specific species and strains from the measurement of DNA duplexes and DNA:RNA hybrids, and to detect single-nucleotide polymorphisms.

Another aspect of the technology is to provide a platform that is amenable to multiplexing and easy integration with electronics for field-deployable devices and high-throughput applications.

Another aspect of the technology is to provide single-molecule detection with extremely high sensitivity.

Another aspect of the technology is to provide a detection apparatus that can be easily integrated with microfluidic systems for sample preparation and delivery.

A further aspect of the technology is to provide a system that is significantly faster, more sensitive, easier to use, more energy efficient, and has a smaller overall form factor than existing sensing techniques.

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only.

DETAILED DESCRIPTION

Referring more specifically to the drawings, for illustrative purposes, embodiments of the sensor platform for single-molecule electrical conductance measurements and methods for rapidly detecting a variety of microbial species; the presence of specific target nucleic acids and other molecules, and the presence of specific serotypes without requiring enzymatic amplification or fluorescent markers are generally shown.

Several embodiments of the technology are described generally in FIG. 1 through FIG. 5 to illustrate the apparatus and methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Figure 1:
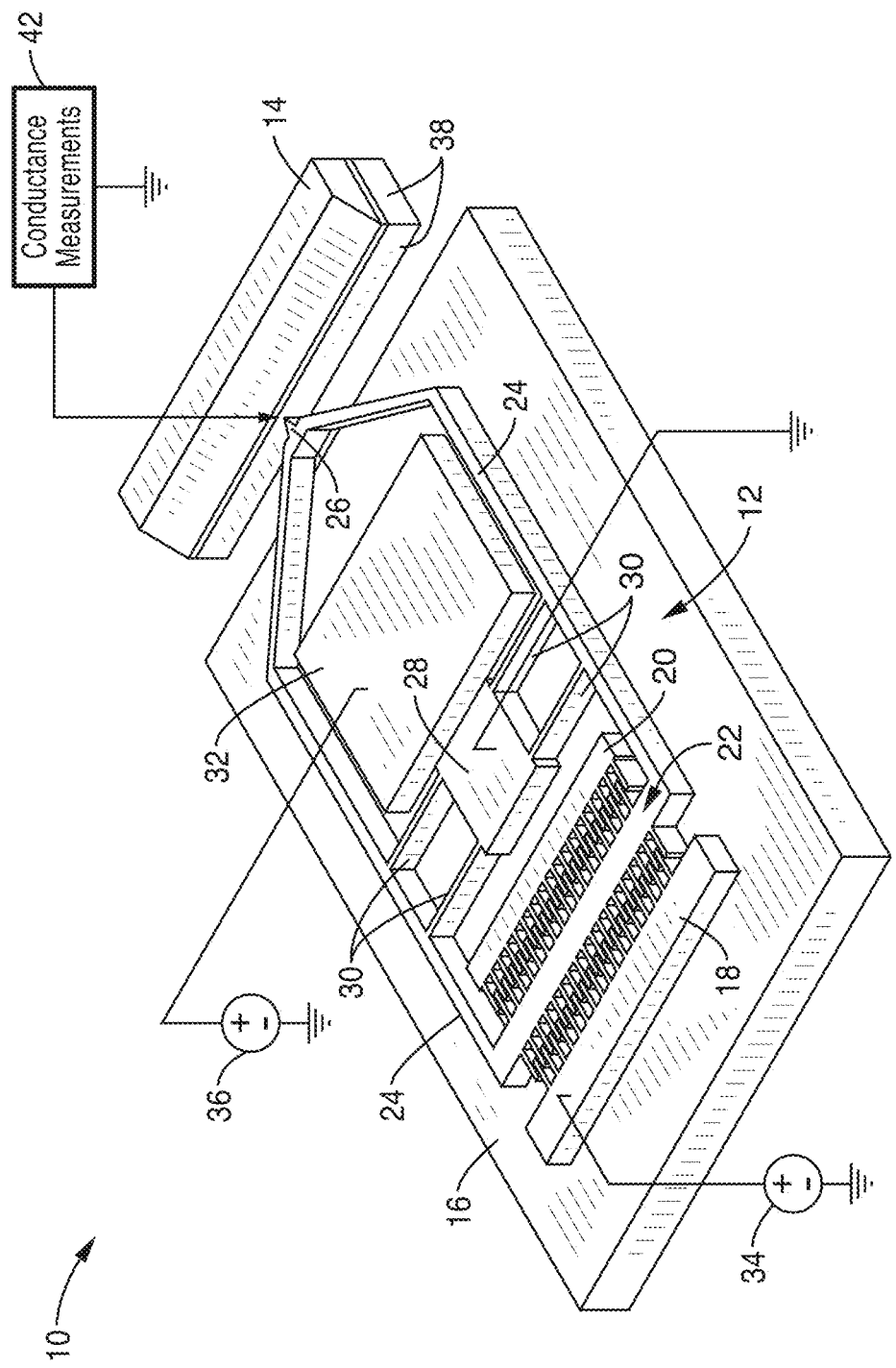
FIG. 1 is a schematic perspective view of a single-molecule conductance measurement platform based on high-dynamic range MEMS actuators according to an embodiment of the technology described herein. Although only a single-actuator measurement platform is shown, the design can be readily incorporated into an array for concurrent measurements of multiple molecules.

Turning now to FIG. 1, a single on-chip micro-electromechanical system (MEMS) based apparatus 10 with an electrode and a MEMS-based actuator mechanism are depicted schematically and not to scale.

The apparatus 10 has two electrodes separated by a gap. The first electrode 12 is the dynamic electrode with at least one conductive tip 26 that is brought into proximity to the second electrode 14 that is a static electrode and does not move in the embodiment shown in FIG. 1. The MEMS-based actuator mechanism is capable of coarse movements with a comb drive and fine movements with a parallel-plate mode actuator that induces horizontal movement of a conductive tip 26.

The dynamic electrode 12 has a base substrate 16 that supports a movable electrode element that is anchored to the base substrate 16 with one or more anchor elements 28. This sliding element 24 of the dynamic electrode 12 moves along a parallel plane to that of the base substrate 16. In the embodiment shown in FIG. 1, the sliding element 24 of the electrode 12 has a generally open rectangular shape with a tapered end with at least one conductive tip 26 and a high dynamic range comb drive 22 at the end opposite of the tip 26. The sliding element 24 is secured to base substrate 16 with an anchor 28 with one or more flexible, resilient arms 30 that orient and stabilize the sliding element 24 and limit the overall linear movement of the sliding element 24 upon actuation of the comb drive portion of the MEMS actuator.

The MEMS actuator of the dynamic electrode preferably has a course movement actuator mechanism and a fine movement actuator mechanism to provide long and short stroke movement of the sliding element 24 and the tip 26 with respect to the electrode surface 38 of the second electrode 14.

The course movement actuator mechanism in the embodiment of FIG. 1 has a bi-directional comb drive 22 with two sets of tines on the sliding element 24. The stationary back bias anchor 18 and front bias anchor 20 have corresponding interdigitating tines with the tines of the sliding element 24.

The comb drive of the MEMS actuator provides long stroke movement of the sliding element 24 and the fine adjustment bias 32 produces a fine stroke movement of the tip 26 of the sliding element 24. The comb drive 22 is connected to a comb drive bias voltage source and a comb drive controller 34. The fine adjustment bias 32 is is connected to a bias voltage source and to a bias voltage source controller 36. In another embodiment, the control over the comb drive 22 and fine adjustment bias 32 is accomplished with a computer processor and programming.

The tip 26 of the tapered end of the sliding element 24 is preferably very sharp (~nm radius) for break-junction measurements to ensure that the current is determined by only a single molecule. In one embodiment, the conductive tip 26 is tapered with an average diameter between approximately 1.5 nm and approximately 2.5 nm.

The fact that the tip 26 is pointing horizontally may make it difficult to fabricate. One multi-step process for creating the point-contact tip begins with patterning of the tapered end of the sliding element 24 with a rectangular protrusion. The device layer of the SOI wafer may then be etched in $XeF_2$, which is a gas-phase isotropic etchant of silicon. The isotropic nature of the etching creates a lateral under-cut while removing silicon vertically. The length and width of the protrusion pattern can be optimized to create a horizontal silicon spike under the protrusion. The residual silicon on top of the buried oxide layer can be removed during the release process. Then, in order to further sharpen the tip 26, the device layer can be thermally oxidized, which converts a thin surface layer of the silicon into silicon dioxide. The oxide layer can then be removed with a buffered oxide etchant (BOE), leaving a very sharp silicon tip. To be able to form single-molecule junctions and provide a conduction path to the wirebond pad, the device layer will then be metalized with gold or other conductive material.

Another important consideration with the formation of the tip 26 is that many of the measurements will take place in aqueous solutions so that the DNA:RNA hybrids, for example, will maintain their proper secondary structure. For many aqueous measurements, special care is taken to avoid leakage currents between the tip 26 of electrode 12 and the secondary flat electrode 14 through the solution. Because the electrochemical leakage current is proportional to the surface area, this procedure limits the leakage current to the order of a few pA. In an alternative embodiment, this problem can be overcome by coating the tip 26 with a wax coating so that only the apex of the tip is exposed.

To overcome this issue in the MEMS-BJ device, in another embodiment, a thin layer of insulation in the form of a thermally grown oxide or a deposited silicon nitride film can be used to cover the electrical pathway from near the apex of the tip to wirebond pad. The exact material and thickness of this insulation layer can be optimized to limit the effect of leakage current on the conductance measurement.

The second electrode of the device 10 is preferably a static electrode 14 that has a smooth electrode surface 38 that is oriented opposite of the conducting tip 26 of the dynamic electrode 12 and separated by a small gap. In one embodiment, the electrode surface 38 has a thin film of a conductive metal such as gold, platinum or titanium. In another embodiment, the surface 28 of static electrode 14 has a corresponding sharp tip oriented opposite to the tip 26 of the dynamic electrode 12. In a third embodiment (not shown), two dynamic electrodes 12 are positioned tip to tip so that the distance between the tips can be varied through actuation of both of the electrodes.

To achieve repeatable, low-noise, single-molecule conductance measurements it is preferable to have either an extremely smooth surface 38 or a second tip as the second electrode 14 in the break-junction measurements. A static electrode 14 with a smooth surface 38 or a second tip is desirable because rough surfaces create many potential current pathways between the two electrodes 12, 14 that obfuscate the exponential current decay that should occur when two metal surfaces are withdrawn.

Figure 2A:
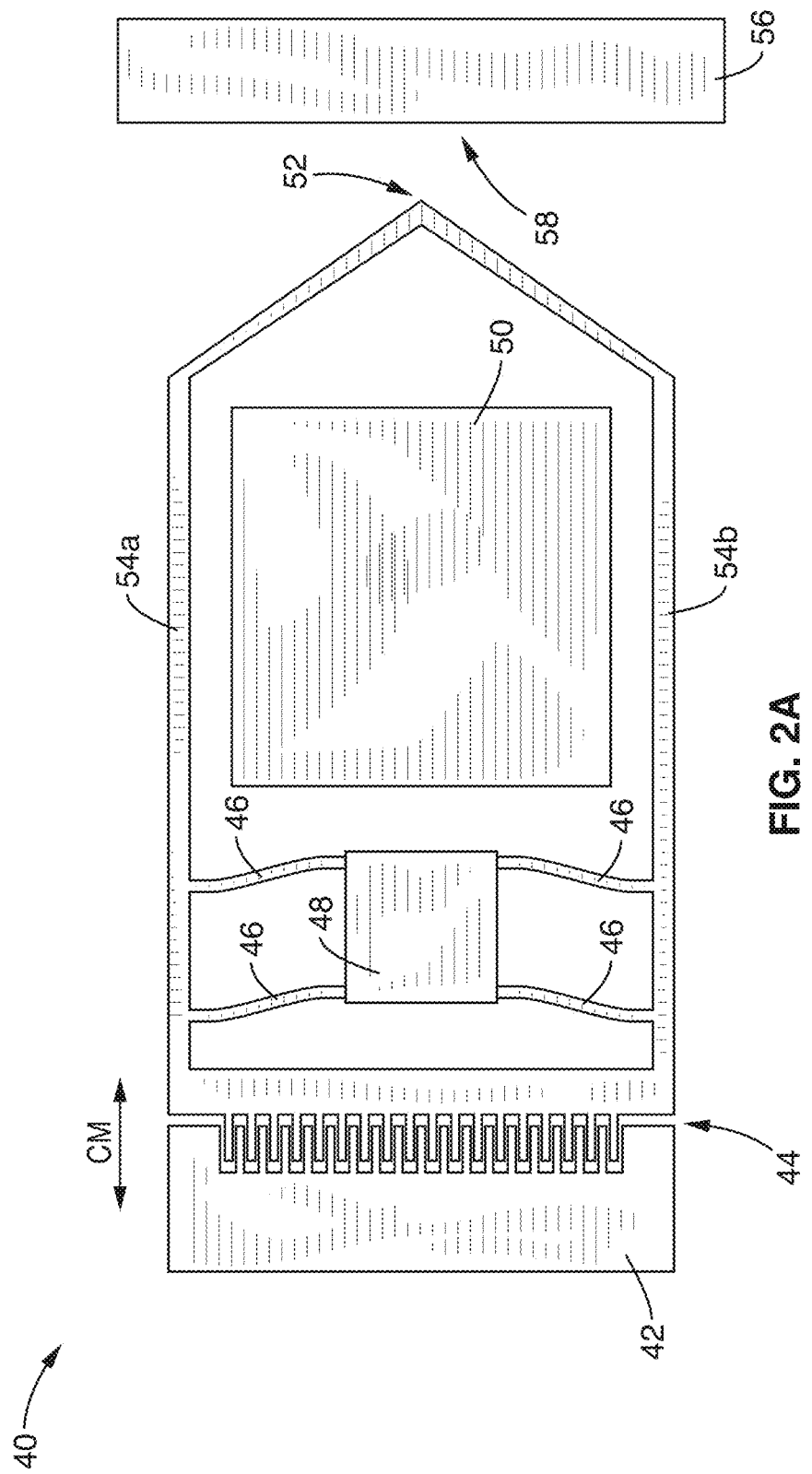
FIG. 2A is a top plan view depicting the coarse movement of the sliding electrode and tip realized by a single comb drive according to one embodiment of the technology.
Figure 2B:
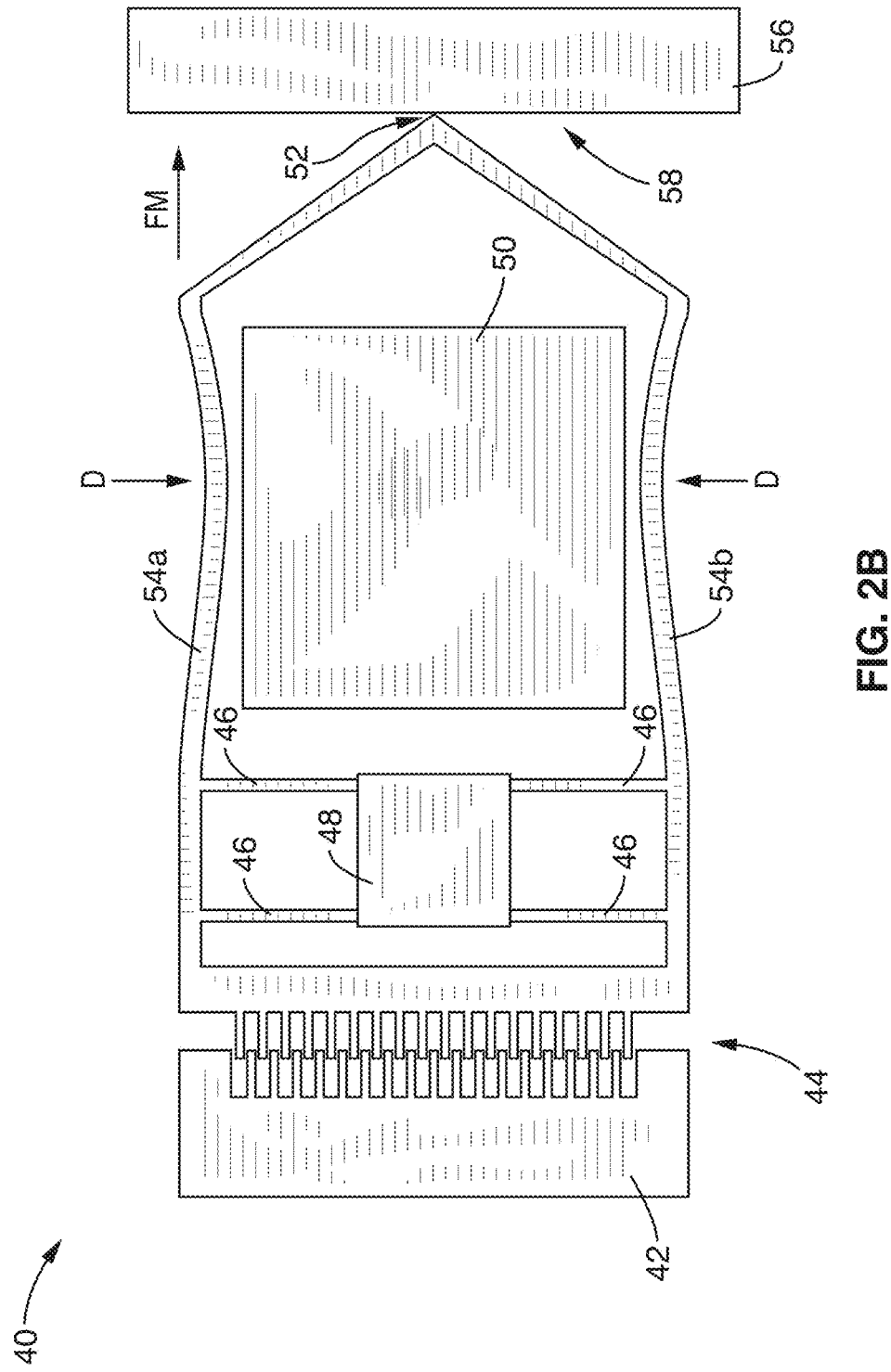
FIG. 2B is a top plan view depicting the fine movement of the sliding electrode and tip of FIG. 2A realized by deflections of a parallel-plate mode actuator.

For the devices shown in FIG. 1 and FIG. 2A and FIG. 2B and the functional demonstrations in the examples, static electrodes with very smooth surfaces were used. Traditionally, microfabricated surfaces with low surface roughness are produced by performing chemical-mechanical polishing on silicon wafers. However, to allow horizontal contact and precise alignment, a more integrated method of fabricating the surface was utilized and wet-etching of silicon in alkaline solutions (e.g. KOH, or TMAH) was used for this purpose. It has been shown that wet-etching silicon in high concentration KOH solutions can produce an extremely smooth surface finish along the (111) crystalline face.

In addition, because these embodiments are designed with two separate components, the static electrode 14 side can be easily replaced without replacing the dynamic electrode 12 side. This feature may be important in certain instantiations of the device. For example, instead of directly adding probe DNA molecules to the solution as part of the extraction protocol, it is possible to place these probes on the electrode 14 smooth surface 38 using a thiol linker. In this case, it will be possible to look for different species or serotypes by simply replacing the static electrode 14 with an electrode that has different probes grafted onto it rather than exchanging the entire MEMS device platform.

Referring now to FIG. 2A and FIG. 2B, an alternative embodiment 40 of the apparatus is shown with a single comb drive 44 to generally illustrate the coarse movement (CM) of the sliding electrode structure upon actuation (FIG. 2A). The comb drive 44 of the system is used to move the entire sliding electrode tip-carriage structure into the range of the flexural system for fine control movement (FM) illustrated in FIG. 2B for break-junction tapping cycles. The travel range of the sliding element upon actuation of the anchor bias 42 and comb drive 44 is determined by the voltage that is applied to the dynamic electrode. A relatively large actuation stroke in the range of approximately 10 μm to approximately 100 μm is preferred for the comb drive 44 of the detection platform 40.

As seen in FIG. 2A, the course movement of the tip 52 away from the second electrode 56 with the activation of the comb drive 44 causes the four resilient support arms 46 of anchor 48 to flex. The forward course movement of the comb drive 44 away from the anchor bias 42 brings the tip 52 in closer proximity to the surface of electrode 56 and the support arms 46 will either no longer flex or will flex in the opposite direction.

Because the length of the target molecules may be on the order of a few nanometers, extremely fine movement resolution is also needed to accurately measure the conductance of a single-molecule using the break-junction approach. The fine movement of the tapered end and tip 52 with respect to the electrode surface 58 of the stationary electrode 56 is illustrated in FIG. 2B.

Once the tip 52 of the sliding element is brought to the proximity of the second electrode 56 with the comb drive 44, the tip 52 is brought into the proper final position by the fine control system. Activation of the fine adjustment bias 50 will result in the deflection of both lateral support beams 54a and 54b of the sliding element and the fine movement of tip 52 toward surface 58 of the static electrode 56 as illustrated in FIG. 2B.

With this second-stage actuation, the fine adjustment bias 50 preferably has an approximately 1 nm/V actuation sensitivity and uses the parallel plate actuator to deform the lateral support beams 54a, 54b thereby moving the conducting tip 52. This fine adjustment bias 50 causes an in-plane deflection (D) of the lateral support beams 54a, 54b that is perpendicular to the direction of the movement of the comb drive 44. At the same time, a slight longitudinal deflection is induced due to the deformation of the beams 54a, 54b moving the tip 52 closer to the surface 58 of the second electrode 56. The dynamic electrode is intentionally made large to accommodate the relatively large horizontal movement of the sliding element. The flexural system may also require a range that is significantly larger than the resolution of the comb drive 44, and preferably has sub-angstrom resolution of the tip 52 movement for performing tapping cycles. In one embodiment, the fine movement actuator mechanism has an actuation stroke in the range of about 0.01 Å to about 0.1 Å.

This design also has the added advantage that the coarse movement is effectively decoupled from the fine movement control. The vertical dimension of the supporting beams 54a, 54b will be large enough to support the mass of the part that carries the conducting tip 52. This arrangement allows the design of a very stiff actuator for improved resolution and noise immunity. The dimensions (length, width, and height) of the supporting beams and sliding element structure can also be optimized to achieve the desired actuation sensitivity and sufficient shock/vibration resistance.

Referring to FIG. 3A through FIG. 3D and FIG. 4A through FIG. 4D, the apparatus can be fabricated as two components, designated as the dynamic electrode and the static electrode and illustrated in FIG. 1 and FIG. 2A and FIG. 2B.

Figure 3A:
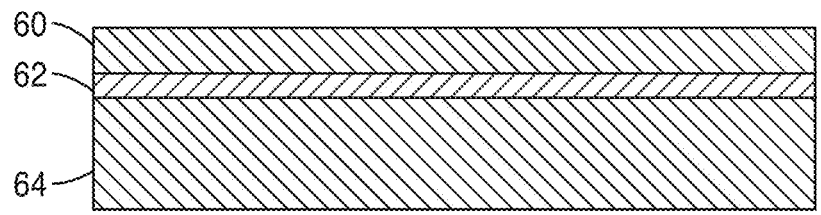
FIG. 3A through FIG. 3D is a schematic flow diagram of one method for fabricating the sliding electrode part of the apparatus of FIG. 1.

To fabricate the dynamic electrode, one preferred process starts with a conventional silicon-on-insulator (SOI) wafer as shown schematically in FIG. 3A. The initial wafer has a device or top silicon layer 60, a middle insulator layer 62 and a base silicon layer 64.

Figure 3B:
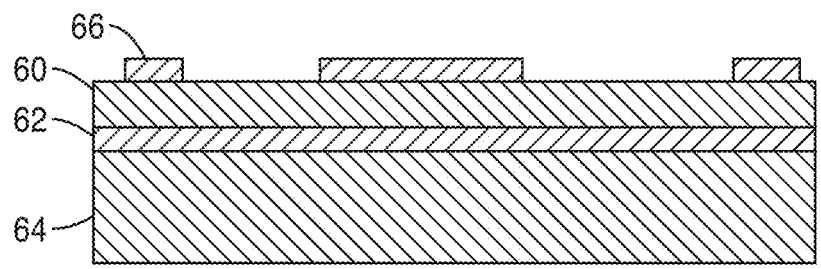

Next, a signal trace is patterned by a sputtering a layer 66 of Ti/Au or some other metal on to the top silicon layer 60 as shown in FIG. 3B.

Figure 3C:
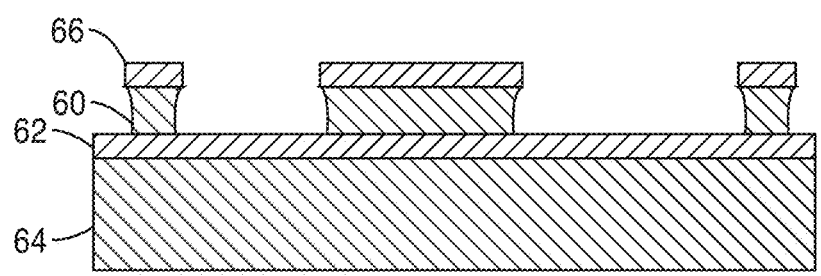

Then, the exposed device layer silicon 60 that is not covered by the patterned signal trace layer 66 is removed by a slightly anisotropic etching method so that a negative sidewall profile is created as seen in FIG. 3C. For example, a well-controlled DRIE etching recipe can be used.

Figure 3D:
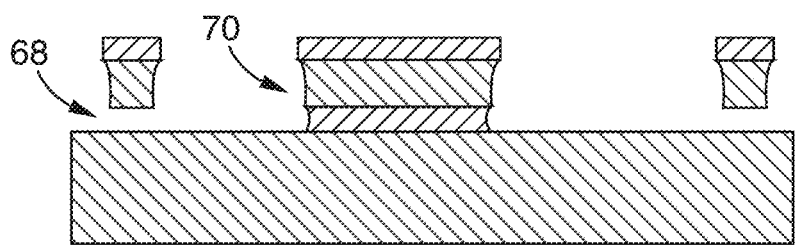

Finally, the remaining buried oxide layer 62 is removed by isotropic etch (e.g. buffered-oxide-etch) as shown in FIG. 3D. Regions with a smaller silicon area will be released due to undercut 68. However, the center anchor area is still attached to the handle oxide layer 70 because its area is larger and is not undercut by the process. In this way, the anchor 48 will not be undercut and remain fixed while the lateral support beams, comb tines, resilient arms 46 and tapered ends of the sliding element will be released from base silicon layer 64 the wafer.

Figure 4A:
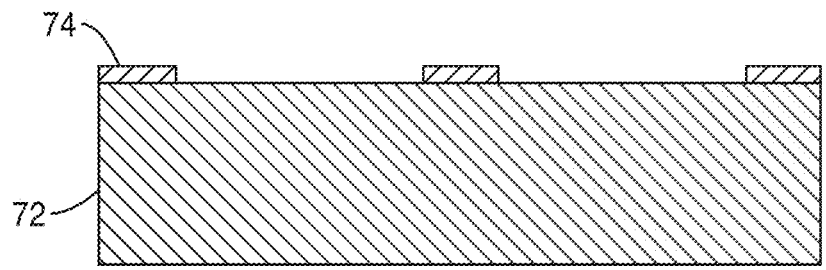
FIG. 4A through FIG. 4D is a schematic flow diagram of one method for fabricating the fixed electrode part of the apparatus of FIG. 1.
Figure 4B:
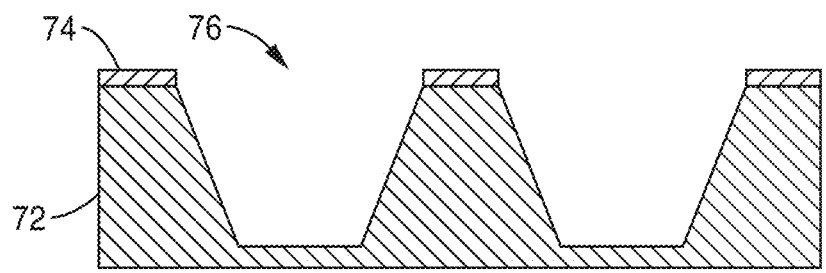

To fabricate the static electrode, the process starts with a silicon wafer 72 that is patterned with a layer 74 of etching mask (e.g. low-stress LPCVD silicon nitride) as shown schematically in FIG. 4A. The patterned wafer is then etched with an anisotropic wet etch of the silicon substrate to remove non-patterned sections 76 of the substrate 72. The wet etch should be well-controlled to result in an extremely flat sidewall surface as seen in FIG. 4B.

Figure 4C:
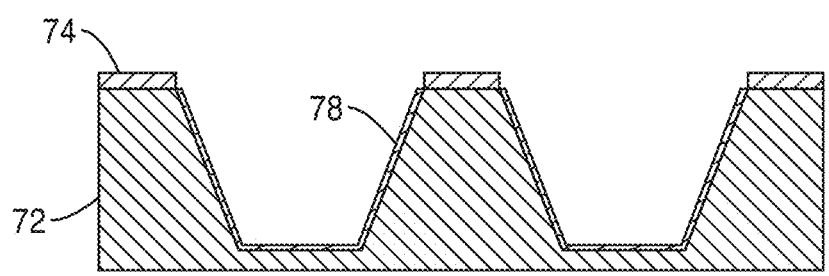
Figure 4D:
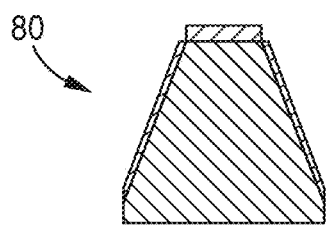

Next, etched surfaces are coated with a conductor 78 (e.g. Ti/Au) to form conductive surfaces as shown in FIG. 4C. Finally, a single electrode device 80 is isolated by force as illustrated in FIG. 4D. The fabricated static electrode 80 is then associated with the dynamic electrode, voltage sources, detectors and controllers to form the single-molecule conductance measurement platform described above. Although only a single-actuator measurement platform is shown, the design can be readily incorporated into an array for concurrent measurement of multiple molecules.

The hardware and software necessary to support the on-chip platform preferably includes a printed circuit board (PCB) with a removable socket for easy replacement of the MEMS-BJ chip and support of the drive and measurement electronics. This board preferably includes a current amplifier that is used to measure the conductance of the molecular junction. The current amplifiers can work in either log-scale or linear-scale supporting a current range from ~100 fA to 1 mA.

The second major component of the electronic hardware included on the PCB is the voltage drivers that are needed to control the mechanical actuators. The MEMS actuator platform of FIG. 1 is generally designed to be very stiff to achieve a high movement resolution. As a result, a high (>200V) absolute actuation voltages may be needed.

In this embodiment, high-voltage driver circuits are integrated with the control electronics to provide stable bias voltages. In one embodiment, the Teledyne DALSA DH9685 high-voltage driver integrated circuit, which can provide up to a 240 V static voltage from a 5-V power supply. With 16-bit resolution, the minimum output voltage step is ~3 mV, which translates into ~1.5 nm movement resolution for the coarse stage (with 100 μm stroke), and 0.03 Å resolution for the fine stage (with 200 nm stroke). The stroke and resolution for each stage is more than sufficient for achieving contact between the two electrodes and performing break-junction measurements. In addition, the DH9685 provides a 96-channel output, making it ideal for extending the instrument into an array form. As extremely sensitive movement control is desired, special attention needs to be paid to power supply noise filtering.

The board may also include input and output ports for interfacing the electronics with the software control system. This aspect includes analog channels for the current amplifier output and applied bias, and a digital bus for the actuator control system. The analog and digital systems are properly isolated to reduce noise.

The software control system preferably includes a control/feedback system and data acquisition modules. Initial testing described in the examples implemented software in LabView with a National Instruments (NI) Data Acquisition (DAQ) card for performing all low-voltage analog to digital (ADC) and digital to analog conversion (DAC) steps. The control system was designed to continuously monitor the output of the current amplifier and use this as a feedback signal to determine the correct electrode separation in the break junction system and adjust the digital bus controlling the actuation voltage drivers. This system can achieve approximately 10 break-junction cycles per second. With a current amplifier that has a bandwidth on the order of 5 kHz, a software sampling rate of 20 kHz, and response time of the mechanical actuator on the order of 10 μs, this goal will be well within the available speeds and resolution of standard NI DAQ cards (e.g. NI PCIe-6353). Achieving this resolution allows the collection of 6000 break junction traces in 10 minutes. These traces can be analyzed in real-time using algorithms to identify which curves have steps. Then they can be added to a conductance histogram to identify the presence of specific RNA sequences in solution, and thus specific microbes. Because of the speed of the tapping cycles, the actual measurement of a sample, once prepared, requires less than 15 minutes.

In another embodiment, the control of the movement of the electrodes is implemented on a microcontroller and the electrodes are connected to an external circuit for single-molecule conductance measurements. Computer control programming of the comb drive 44 and fine drive bias 50 and the conductance measurements 42 may also include display, computing and recording functions.

It can be seen that the apparatus can be adapted to measure the conductance of a wide variety of molecular systems including alkanedithiols, benzenedithiol, molecular diodes, nucleic acids, DNA:RNA hybrids and amino acids. Importantly, in the case of oligonucleotides the conductance is extremely sensitive to the sequence, and even single-nucleotide polymorphisms can be identified.

The technology described herein may be better understood with reference to the accompanying examples, which are intended for purposes of illustration only and should not be construed as in any sense limiting the scope of the technology described herein as defined in the claims appended hereto.

Example 1

To demonstrate the detector system, a MEMS based break-junction (MEMS-BJ) platform with sub-angstrom mechanical control for measuring the conductance was fabricated and tested. The functionality of this MEMS-based tool was illustrated by measurements of the conductance of molecular RNA targets bound to complementary DNA probes that will ultimately allow the detection of a variety of microbial species.

The platform structure of FIG. 1 was fabricated with a bidirectional comb drive, a parallel-plate mode actuator, and a gold plated conductive tip that could be brought into close proximity to a perpendicular flat second electrode. The comb drive had a stroke range of approximately 100 μm providing coarse movement of the dynamic electrode. The parallel-plate mode actuator provided fine movement of the tip with a resolution of approximately 0.03 Å.

Once the MEMS-BJ chip, the supporting PCB board, and software were completed, a series of calibration steps were performed. The total stroke of the two actuator stages, the sensitivity of the fine-movement system, the bandwidth of the electronics, and the response time of the complete system were quantified.

The coarse actuator stroke range was determined by observing the movement under an optical microscope to determine the total displacement over the voltage range. However, this procedure did not permit a determination of the absolute sensitivity of the fine-movement flexural actuation system used during the break-junction tapping cycles. To determine this sensitivity, the system was calibrated using the Au—Au quantum point contact (QPC). The conductance of a single gold atom is $G_0$ ($G_0=2e^2/h=77.48$ μS), and the length of the Au—Au bond is known to be about 0.23 nm. Multiple gold atoms can be pulled out in a chain in a break-junction device before the junction eventually breaks down, and the current drops to zero. By measuring the length of the $G_0$ conductance steps in thousands of conductance vs. distance traces from a Au quantum point contact (QPC), it is possible to obtain a histogram of the most-likely break-down points of the Au QPC, which occur at integer numbers of atoms. By correlating the distance between the two peaks with the ramp rate of the modulation voltage applied during break-junction experiment it was possible to determine the absolute sensitivity of the mechanical system and compare this to the designed value.

The bandwidth of the overall system was also determined. When very small DC currents (<nA) are involved, systems are often limited by the bandwidth of the current-to-voltage amplifier. But at high currents (>μA), this system may be limited by mechanical response. The limitations of the system bandwidth were determined in two steps. First, the bandwidth of the current amplifiers was determined by acquiring a Bode plot of the amplifier gain as a function of the applied current frequency. Second, a voltage step function (rise time ~50 ns) was applied to the fine-control actuators to move them away from the surface as quickly as possible to determine if the electronic bandwidth or mechanical bandwidth dominate the characteristics of the system. The current between the dynamic electrode tip and the second electrode decreases exponentially as the electrodes separate. By finding the time constant for this decay and comparing it to the cut-off frequency of the current amplifiers it was possible to determine if the electrical system or mechanical system dominates the total system response.

Finally, the stability of the device was also evaluated using a large time-constant feedback controller to maintain a fixed tunneling voltage between the tip and the surface and measuring the noise spectrum of the current to determine the absolute stability of the device, and to determine if any of the mechanical modes in the device decrease the stability of the system. Evaluation of the mechanical and electrical limitations of the system will help in the design of the software control system to ensure the break-junction measurements proceed as rapidly as possible and to maximize the stability and response time of the system.

Example 2

In order to assess the functionality of the MEMS-BJ device, the capability of the device for performing single-molecule conductance measurements was tested. These tests demonstrated that it is possible to measure the conductance of oligonucleotide duplexes at the single-molecule level, that the conductance is sensitive to changes in length and sequence, that the target nucleic acid is stable enough to be detected in this fashion, and that the targeted molecules provide sufficient specificity that the conductance measurements will be able to discriminate between species and even strains or serotypes within a species.

Preliminary evaluations measured conductance of DNA duplexes and DNA:RNA hybrids, and detected single-nucleotide polymorphisms with Scanning Tunneling Microscope (STM)-break junction or Mechanically Controlled Break Junction (MCBJ) devices. Target RNA fragments were hybridized with complementary DNA sequences that were capable of binding to gold electrodes. Because the conductance is sensitive to single-nucleotide polymorphisms, this technique was capable of strain-level identification of microbes.

The (STM)-break junction system evaluation proceeded by bringing the atomically sharp STM-tip down into contact with the substrate electrode in the presence of the molecules of interest. These molecules were constructed so that they were capable of binding to both electrodes through appropriate linker groups. In this case, a DNA probe was used with either amines or thiols on each terminus to provide the binding. Once contact was made between the two electrodes, as can be determined from the current, the tip was withdrawn until the current reaches the resolution of the current amplifier (~pA). If molecules were bound between the two electrodes during the separation process, then steps occurred in the observed current vs. distance trace. By repeating this process hundreds or thousands of times, it was possible to perform a statistical analysis of the results to determine the most probable conductance of a single molecule junction.

Importantly, in the case of oligonucleotides the conductance was shown to be extremely sensitive to the sequence, and even single-nucleotide polymorphisms could be identified. The conductance values of two sequences that differ by only a single base can be different by as much as 10 times. This observation verifies that if used for detection systems, the conductance value will indicate not only if a species is present, but it will also be able to discern between subspecies using the same DNA probe.

The (STM)-break junction system approach was also used to measure the conductance of DNA:RNA hybrids, and to verify that biologically relevant RNA sequences can be measured using this technique. In this illustration, a 15 base sequence from the 16S gene transcript from O157:H7 *E. coli* was used and paired with a complementary probe DNA with amine linkers. Both oligomers were synthesized and purified by commercial vendors, and then hybridized prior to conductance measurements.

The resulting conductance histogram showed a clear peak near $9\times10^{-5}G_0$. The results demonstrated that biologically relevant sequences can be measured. A control experiment performed on RNA extracted from an *E. coli* colony without the DNA probe molecules present indicated that interference from non-target oligomers was minimal.

In addition, in order for the MEMS-BJ based detection method to be effective, the RNA target should be stable enough to remain intact until measurements are performed, otherwise it may go undetected. RNA is highly sensitive to turn-over and degradation, a feature that enables the rapid adaptation of cells to new or altered stimuli.

To evaluate bacterial RNA stability in environmental samples, $10^8$ *E. coli* O157:H7 cells were innoculated onto lettuce plants and the plants were incubated under temperatures and relative humidity resembling that found in agricultural fields. Similar to other reports of *E. coli* O157:H7 on plants, this organism did not survive well on the lettuce plants and the numbers of viable cells that were able to form a colony on agar medium declined to 1000 cells per leaf within 48 hours. However, enumeration of *E. coli* O157:H7 on the same lettuce plants by RT-qPCR showed very modest (10-fold) reductions in total *E. coli* O157:H7 numbers on the plants even after four days. Notably, this level of detection occurred even though the total *E. coli* O157:H7 RNA recovered from the plant degraded over time. Hence, bacterial RNA is very stable in complex environments such as plant leaf surfaces, even when the target cells are unable to reproduce on laboratory culture medium.

Accordingly, the on-chip micro-electromechanical system (MEMS) is capable of performing single-molecule conductance measurements that can be used to measure the electrical conductance of short fragments of RNA or other markers extracted from microbial cells to detect and identify the presence of specific serotypes rapidly without requiring enzymatic amplification.

Example 3

The MEMS based break-junction (MEMS-BJ) platform with sub-angstrom mechanical control was used to measure the conductance of single RNA:DNA hybrid molecules to directly identify specific microbes of interest. The detection platform was used to demonstrate direct detection of one gram-negative (*Escherichia coli*) and one gram-positive (*Lactobacillus plantarum*) bacterial species. The capacity to detect both organisms is of importance for food production because *E. coli* is a potentially harmful species that can contaminate fresh produce and *L. plantarum* is a beneficial organism essential for producing fermented foods.

To further demonstrate the MEMS-BJ single-molecule conductance platform, the system was used to identify short fragments of the 16S rRNA gene transcript, a small subunit of ribosomal RNA from bacteria, as an illustration of the specificity of the system to uniquely identify serotypes of microbial species. The MEMS-BJ platform provides the opportunity to detect and monitor specific bacterial taxa in communities of other (micro)organisms and in complex detecting environments.

An important facet of bacterial monitoring in complex environments is the selection of the specific target molecules for detection. Because the 16S rRNA gene is common to all bacteria, the technique will be capable of identifying any species once appropriate target fragments of the 16S rRNA gene or other target molecules are identified. The 16S rRNA gene is shared among all bacteria and is typically the preferred marker for bacterial molecular phylogenetic analysis. By targeting 16S rRNA gene transcripts, for example, detection will be enhanced by the high proportion of rRNA to mRNA transcripts in bacterial cells such that rRNA typically constitutes >90% of total nucleic acid content.

Although the 16S rRNA gene is the target here, the MEMS-BJ device can be subsequently applied to detect other bacterial gene transcript targets (e.g. metabolic or virulence genes) that are functionally relevant but present in lower quantities as well as RNAs specific to other microorganisms and viruses.

The ubiquity of the 16S rRNA in microbial systems makes it an ideal target. A device that can target precise regions of the 16S rRNA that is specific enough to provide species or even sub-species information rapidly without the use of conventional amplification protocols will be broadly applicable to any field in biology where sample bacteria need to be quickly identified. This includes pathogen identification for health-care and national security, monitoring beneficial bacteria in the human microbiome, and microbial monitoring in the production and processing of foods where national outbreaks of food-borne pathogens have become an increasingly common occurrence.

Figure 5:
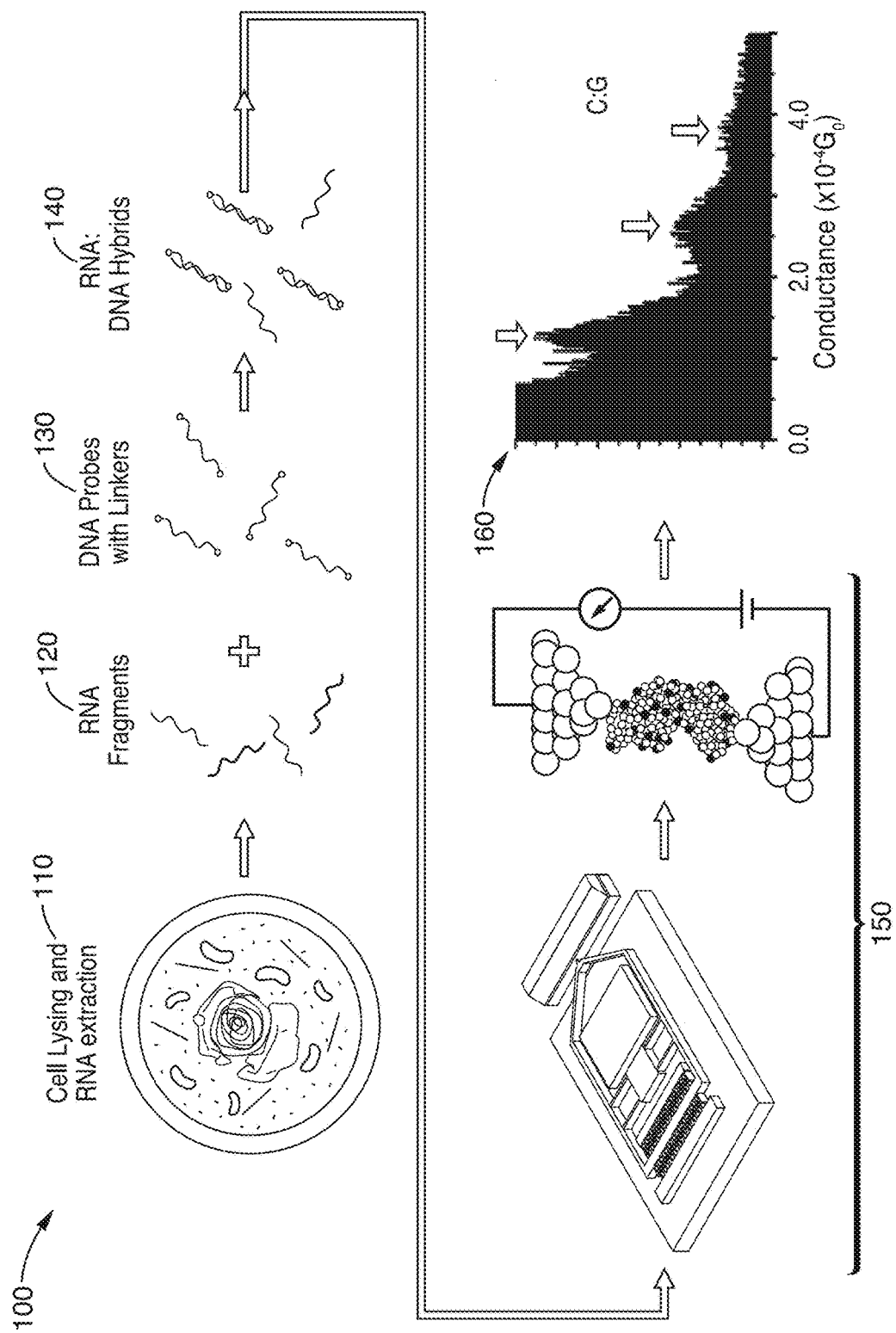
FIG. 5 is a schematic flow diagram of a process for using a MEMS based break-junction (MEMS-BJ) platform with sub-angstrom mechanical control for measuring the conductance of single RNA:DNA hybrid molecules to directly identify microbes of interest according to one embodiment of the technology.

As shown generally in FIG. 5, the detection process 100 in this embodiment begins by lysing and extracting RNA fragments 110 from the sample cells of interest. The lysate or extracted RNA fragments 120 is mixed with corresponding DNA probes 130 to form DNA:RNA hybrids 140 and all single-stranded material is then digested. The DNA probes 130 that are complementary to species-specific RNA fragments 120 have chemical linkers that are capable of binding to the gold electrodes. Preferably, the DNA probe 130 will have either amines or thiols on each terminus as chemical linkers to provide the binding functionality.

This mixture of hybrids is then introduced into a MEMS-based break junction device 150 that is capable of rapidly performing single-molecule conductance measurements. The device brings the atomically sharp tip down in contact with the stationary electrode in the presence of the molecules of interest. Contact between the electrodes can be determined by observing the current. Once the contact is made between the two electrodes, the tip is withdrawn until the current reaches the resolution of the current amplifier (~pA). If molecules bind between the two electrodes during the separation process, then steps occur in the current vs. distance trace.

Once multiple conductance measurements are performed in this manner, a conductance histogram 160 verifying the molecule of interest is present will be obtained. By repeating this process many times, it is possible to perform a statistical analysis of the results to determine the most probable conductance of a single molecule junction.

The technique shown generally in FIG. 5 is capable of measuring the conductance of DNA duplexes and DNA:RNA hybrids 140 that are less than ~20 base pairs in length. The conductance of these molecules is extremely sensitive to length, sequence, and single-nucleotide polymorphisms, and as such, it will be capable of serotype-level accuracy. Moreover, because this technique is sensitive to single-molecule events, it will only require a small-number of detection events (typically on the order of 200 molecules) to positively identify the presence of a specific molecular species.

The utility of the device for detecting bacteria in complex environments was further illustrated by using 16S rRNA transcripts to determine the diversity of bacteria in the digestive tracts of mice that were fed either a high fat/high sucrose diet or a low fat/high plant polysaccharide chow. A fraction of those mice were fed $10^9$ cells of *Lactobacillus plantarum* WCFS1, a beneficial microbe that is consumed in fermented foods and beverages. Then, 16S rRNA transcript cDNAs were used for amplicon-based HTP sequencing. The detection experiments showed dramatic and significant changes among the intestinal microbiota in response to the mouse diet. For example, indigenous populations of *Lactobacillus*, and specifically, *Lactobacillus gasseri* strains were significantly reduced in mice fed the high fat/high sucrose diet.

Moreover, it was possible to detect the fed *L. plantarum* inoculant even among the background of approximately $10^{10}$ indigenous bacterial cells that were present in the intestine. The *L. plantarum* numbers were also enriched in mice fed the high fat/high sucrose diet. It can be seen that the knowledge from 16S rRNA gene surveys such as those performed here can be directly used to design and detect bacteria with diagnostic, health-associated, or practical significance, such as indigenous and dietary *Lactobacillus*, among large numbers of human individuals without the need for comprehensive approaches such as HTP DNA sequencing. Similarly, metagenome and meta-transcriptome sequence data are sources for MEMS-BJ applications to target functional gene transcripts, viruses, or other microorganisms.

From the description herein, it will be appreciated that that the present disclosure encompasses multiple embodiments which include, but are not limited to, the following:

1. A single-molecule conductance measurement apparatus, the apparatus comprising: (a) a MEMS-based actuator; (b) a conductive needle electrode coupled to the MEMS-based actuator; and (c) a second electrode having a smooth surface; (d) wherein the conductive needle electrode is configured to make contact with the smooth surface of the second electrode; and (e) wherein the conductive needle electrode is moveable in positional relation to the smooth surface of the second electrode by the MEMS-based actuator.

2. The apparatus of any preceding embodiment, further comprising: an electrical conductivity detector coupled to the electrodes and a display.

3. The apparatus of any preceding embodiment, wherein the MEMS-based actuator comprises: a course movement actuator mechanism and a fine movement actuator mechanism.

4. The apparatus of any preceding embodiment, wherein the course movement actuator mechanism has an actuation stroke in the range of about 10 µm to about 100 µm to bring a conductive needle electrode tip in proximity to the second electrode.

5. The apparatus of any preceding embodiment, wherein the fine movement actuator mechanism has an actuation stroke in the range of about 0.01 Å to about 0.1 Å.

6. The apparatus of any preceding embodiment, wherein the course movement actuator mechanism comprises: a comb drive; a comb drive bias; and a comb drive bias controller configured to control actuation of the comb drive and position of the conductive needle electrode.

7. The apparatus of any preceding embodiment, wherein the fine movement actuator mechanism comprises: a parallel plate actuator; a fine adjustment bias; and a fine adjustment bias controller configured to control actuation of the parallel plate actuator and position of a conductive needle electrode tip in relation to the smooth surface of the second electrode.

8. The apparatus of any preceding embodiment, wherein the parallel plate actuator has an actuation sensitivity of ~1 nm/V.

9. The apparatus of any preceding embodiment, wherein the needle electrode tip is coated with a conductive metal.

10. A single-molecule conductance measurement apparatus, comprising: (a) an array of one or more detector platforms, each detector platform comprising: (i) a stationary electrode; and (ii) a dynamic electrode coupled to a MEMS-based actuator with at least one conductive tip configured to move in positional relation to the stationary electrode by the MEMS-based actuator; (b) a controller operably coupled to the MEMS-based actuator of each detector platform; and (c) an electrical conductivity detector configured to detect conductance between the stationary and dynamic electrodes of each detector platform; (d) wherein single-molecule conductance measurements are controlled by contact and withdrawal of the conductive tip of the dynamic electrode with the stationary electrode by the controller.

11. The apparatus of any preceding embodiment, wherein the MEMS-based actuator of each platform comprises: a course movement actuator mechanism; and a fine movement actuator mechanism.

12. The apparatus of any preceding embodiment, wherein the course movement actuator mechanism comprises: a comb drive; and a comb drive bias coupled to the controller, the controller configured to control actuation of the comb drive and a position of the conductive tip of the dynamic electrode.

13. The apparatus of any preceding embodiment, wherein the course movement actuator mechanism has an actuation stroke in the range of about 10 µm to about 100 µm to bring a conductive dynamic electrode tip in proximity to the stationary electrode.

14. The apparatus of any preceding embodiment, wherein the fine movement actuator mechanism comprises: a parallel plate actuator; and a fine adjustment bias coupled to the controller; the controller configured to control actuation of the parallel plate actuator and a position of a conductive dynamic electrode tip in relation to the smooth surface of the second electrode.

15. The apparatus of any preceding embodiment, wherein the fine movement actuator mechanism has an actuation stroke in the range of about 0.01 Å to about 0.1 Å.

16. The apparatus of any preceding embodiment, wherein the dynamic electrode further comprises: a base support; and an anchor mounted the base support, the electrode coupled to the anchor with one or more resilient arms.

17. The apparatus of any preceding embodiment, wherein the conductive tip is coated with a conductive metal selected from the group of gold, platinum and titanium.

18. The apparatus of any preceding embodiment, wherein the conductive tip is tapered with an average diameter between 1.5 nm and 2.5 nm.

19. A single-molecule conductance measurement apparatus, comprising: (a) an array of one or more detector platforms, each detector platform comprising: (i) a stationary electrode; and (ii) a dynamic electrode with a course movement actuator mechanism, a fine movement actuator mechanism and at least one conductive tip configured to move in positional relation to the stationary electrode by the actuator mechanisms; (b) an electrical conductivity detector configured to detect conductance between the stationary and dynamic electrodes of each detector platform; (c) a computer processor operably coupled to the electrical conductivity detector, and the course and fine movement actuator mechanisms of each detector platform; and (d) a non-transitory computer-readable memory storing instructions executable by the computer processor; (e) wherein the instructions, when executed by the computer processor, perform steps comprising: (i) actuating the course movement actuator mechanism to bring the conductive tip of the dynamic electrode in proximity to the stationary electrode; (ii) actuating the fine movement actuator mechanism to bring the conductive tip of the dynamic electrode in contact with the stationary electrode; (iii) repeatedly contacting and withdrawing the conductive tip of the dynamic electrode with the stationary electrode of each platform in the presence of target molecules; and (iv) measuring electrical conductance across electrodes of each platform over time.

20. The apparatus of any preceding embodiment, the computer processor further comprising a display, wherein the electrical conductance measurements are displayed on the display.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A single-molecule conductance measurement apparatus, comprising:
(a) an array of one or more detector platforms, each detector platform comprising:
  (i) a single stationary electrode; and
  (ii) a dynamic electrode coupled to a MEMS-based actuator with a single least one conductive tip configured to move in positional relation to the stationary electrode by the MEMS-based actuator;
(b) a controller operably coupled to the MEMS-based actuator of each detector platform; and
(c) an electrical conductivity detector configured to detect conductance between the stationary and dynamic electrodes of each detector platform;
(d) wherein single-molecule conductance measurements are controlled by contact and withdrawal of the conductive tip of the dynamic electrode with the stationary electrode by the controller.

2. The apparatus of claim 1, wherein the MEMS-based actuator of each platform comprises:
a coarse movement actuator mechanism; and
a fine movement actuator mechanism.

3. The apparatus of claim 2, wherein the coarse movement actuator mechanism comprises:
a comb drive; and
a comb drive bias coupled to the controller, the controller configured to control actuation of the comb drive and a position of the conductive tip of the dynamic electrode.

4. The apparatus of claim 2, wherein the coarse movement actuator mechanism has an actuation stroke in the range of about 10 μm to about 100 μm to bring a conductive dynamic electrode tip in proximity to the stationary electrode.

5. The apparatus of claim 2, wherein the fine movement actuator mechanism comprises:
a parallel plate actuator; and
a fine adjustment bias coupled to the controller, the controller configured to control actuation of the parallel plate actuator and a position of the conductive dynamic electrode tip in relation to a surface of the stationary electrode.

6. The apparatus of claim 5, wherein the parallel plate actuator has an actuation sensitivity of ~1 nm/V.

7. The apparatus of claim 2, wherein the fine movement actuator mechanism has an actuation stroke in the range of about 0.01 Å to about 0.1 Å.

8. The apparatus of claim 2, wherein the dynamic electrode further comprises:
a base substrate; and
an anchor mounted upon the base substrate, the electrode coupled to the anchor with one or more resilient arms;
wherein the anchor remains stationary while the dynamic electrode moves in positional relation to the stationary electrode.

9. The apparatus of claim 2, wherein each of the conductive tips is coated with a conductive metal selected from the group consisting of gold, platinum and titanium.

10. The apparatus of claim 2, wherein each of the conductive tips is tapered with an average diameter between 1.5 nm and 2.5 nm.

11. A single-molecule conductance measurement apparatus, comprising:
(a) an array of one or more detector platforms, each detector platform comprising:
  (i) a stationary electrode; and
  (ii) a dynamic electrode with a coarse movement actuator mechanism, a fine movement actuator mechanism and at least one conductive tip configured to move in positional relation to the stationary electrode by the actuator mechanisms;
(b) an electrical conductivity detector configured to detect conductance between the stationary and dynamic electrodes of each detector platform;
(c) a computer processor operably coupled to the electrical conductivity detector, and the coarse and fine movement actuator mechanisms of each detector platform; and
(d) a non-transitory computer-readable memory storing instructions executable by the computer processor;
(e) wherein the instructions, when executed by the computer processor, perform steps comprising:
  (i) actuating the coarse movement actuator mechanism to bring the conductive tip of the dynamic electrode in proximity to the stationary electrode;
  (ii) actuating the fine movement actuator mechanism to bring the conductive tip of the dynamic electrode in contact with the stationary electrode;
  (iii) repeatedly contacting and withdrawing the conductive tip of the dynamic electrode with the stationary electrode of each platform in the presence of target molecules; and
  (iv) measuring electrical conductance across electrodes of each platform over time.

12. The apparatus of claim 11, the computer processor further comprising a display, wherein the electrical conductance measurements are displayed on the display.

13. The apparatus of claim 11, wherein the coarse movement actuator mechanism comprises:
a comb drive; and
a comb drive bias coupled to the computer processor, the computer processor configured to control actuation of the comb drive and a position of the conductive tip of the dynamic electrode.

14. The apparatus of claim 11, wherein the coarse movement actuator mechanism has an actuation stroke in the range of about 10 μm to about 100 μm to bring a conductive dynamic electrode tip in proximity to the stationary electrode.

15. The apparatus of claim 11, wherein the fine movement actuator mechanism comprises:
   a parallel plate actuator; and
   a fine adjustment bias coupled to the controller, the controller configured to control actuation of the parallel plate actuator and a position of a conductive dynamic electrode tip in relation to a surface of the stationary electrode.

16. The apparatus of claim 15, wherein the parallel plate actuator has an actuation sensitivity of ~1 nm/V.

17. The apparatus of claim 11, wherein the fine movement actuator mechanism has an actuation stroke in the range of about 0.01 Å to about 0.1 Å.

18. The apparatus of claim 11, wherein the dynamic electrode further comprises:
   a base support; and
   an anchor mounted the base support, the electrode coupled to the anchor with one or more resilient arms.

19. The apparatus of claim 11, wherein the conductive tip is coated with a conductive metal selected from the group consisting of gold, platinum and titanium.

20. The apparatus of claim 11, wherein the conductive tip is tapered with an average diameter between 1.5 nm and 2.5 nm.

* * * * *